United States Patent
Smith, III et al.

(10) Patent No.: US 9,428,719 B2
(45) Date of Patent: Aug. 30, 2016

(54) PERSONAL CARE ARTICLES HAVING MULTIPLE ZONES WITH COMPLIANT PERSONAL CARE COMPOSITIONS

(75) Inventors: Edward Dewey Smith, III, Mason, OH (US); Shawn David McConaughy, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 384 days.

(21) Appl. No.: 13/585,873

(22) Filed: Aug. 15, 2012

(65) Prior Publication Data

US 2013/0043145 A1    Feb. 21, 2013

Related U.S. Application Data

(60) Provisional application No. 61/523,824, filed on Aug. 15, 2011.

(51) Int. Cl.
| | |
|---|---|
| *A47K 7/02* | (2006.01) |
| *C11D 17/04* | (2006.01) |
| *A61Q 19/00* | (2006.01) |
| *A61Q 19/10* | (2006.01) |
| *A61Q 5/02* | (2006.01) |
| *A61Q 5/12* | (2006.01) |
| *A61Q 9/02* | (2006.01) |
| *A61K 8/02* | (2006.01) |
| *A45D 40/00* | (2006.01) |
| *A45D 40/24* | (2006.01) |

(52) U.S. Cl.
CPC ............ *C11D 17/049* (2013.01); *A61K 8/0204* (2013.01); *A61Q 5/02* (2013.01); *A61Q 5/12* (2013.01); *A61Q 9/02* (2013.01); *A61Q 19/00* (2013.01); *A61Q 19/002* (2013.01); *A61Q 19/10* (2013.01); *A45D 40/00* (2013.01); *A45D 40/0081* (2013.01); *A45D 40/24* (2013.01); *A61K 2800/87* (2013.01); *A61K 2800/88* (2013.01)

(58) Field of Classification Search
CPC ........... A61Q 5/02; A61Q 9/02; A61Q 19/10; A61Q 19/002; A61K 8/0204; A61K 8/0208
USPC ....................... 401/201; 15/103.94
See application file for complete search history.

(56) References Cited

U.S. PATENT DOCUMENTS

| | | | |
|---|---|---|---|
| 3,674,374 A | * | 7/1972 | Jennings ........................... 401/8 |
| 3,689,437 A | | 9/1972 | McLaughlin |
| 3,949,137 A | | 4/1976 | Akrongold |

(Continued)

FOREIGN PATENT DOCUMENTS

| | | |
|---|---|---|
| CA | 2012123 | 9/1990 |
| CA | 2012124 | 9/1990 |

(Continued)

OTHER PUBLICATIONS

U.S. Appl. No. 61/620,213, filed Apr. 4, 2012, Smith et al.

(Continued)

*Primary Examiner* — Jennifer C Chiang

(57) ABSTRACT

A personal care article is disclosed having a first compliant personal care composition in a first zone and a second compliant personal care composition in a second zone such that the first and second zones are defined by one or more barriers. Methods for increasing lather are also disclosed herein.

17 Claims, 4 Drawing Sheets

(56) References Cited

U.S. PATENT DOCUMENTS

| | | | |
|---|---|---|---|
| 4,181,632 A | 1/1980 | Schebece |
| 4,207,198 A | 6/1980 | Kenkare |
| 4,328,131 A | 5/1982 | Carson |
| 4,335,025 A | 6/1982 | Barker |
| 4,515,703 A | 5/1985 | Haq |
| 4,554,097 A | 11/1985 | Schebece |
| 4,654,158 A | 3/1987 | Shepherd |
| 4,735,739 A | 4/1988 | Floyd |
| 4,812,253 A | 3/1989 | Small |
| 4,861,508 A | 8/1989 | Wegener |
| 4,953,250 A | 9/1990 | Brown |
| 4,987,632 A | 1/1991 | Rowe |
| 5,066,494 A | 11/1991 | Becher |
| 5,132,115 A | 7/1992 | Wolter |
| 5,225,097 A | 7/1993 | Kacher |
| 5,227,086 A | 7/1993 | Kacher |
| 5,262,079 A | 11/1993 | Kacher |
| 5,264,144 A | 11/1993 | Moroney |
| 5,264,145 A | 11/1993 | French |
| 5,308,180 A | 5/1994 | Pournoor |
| 5,312,559 A | 5/1994 | Kacher |
| 5,340,492 A | 8/1994 | Kacher |
| 5,387,362 A | 2/1995 | Tollens |
| 5,433,883 A | 7/1995 | Massaro |
| 5,433,894 A | 7/1995 | Massaro |
| 5,482,643 A | 1/1996 | Chambers |
| 5,520,840 A | 5/1996 | Massaro |
| 5,523,017 A | 6/1996 | Moran |
| 5,540,854 A | 7/1996 | Fair |
| 5,683,971 A | 11/1997 | Rose |
| 5,683,973 A | 11/1997 | Post |
| 5,698,475 A | 12/1997 | Vlasblom |
| 5,702,992 A | 12/1997 | Martin |
| 5,703,025 A | 12/1997 | Zyngier |
| 5,756,438 A | 5/1998 | Rau |
| 5,786,311 A | 7/1998 | Zyngier |
| 5,888,953 A | 3/1999 | Harris |
| 5,916,856 A | 6/1999 | Massaro |
| 5,968,852 A | 10/1999 | Vlasblom |
| 5,972,860 A | 10/1999 | Eshita |
| 5,985,808 A | 11/1999 | He |
| 6,028,042 A | 2/2000 | Chambers |
| 6,153,208 A | 11/2000 | McAtee |
| 6,162,457 A | 12/2000 | Martz |
| 6,206,863 B1 | 3/2001 | Skewes |
| 6,245,343 B1 | 6/2001 | Roulier |
| 6,322,801 B1 | 11/2001 | Lorenzi |
| 6,328,811 B1 | 12/2001 | Martin |
| 6,376,046 B1 | 4/2002 | Hoshino |
| 6,391,835 B1 | 5/2002 | Gott |
| 6,428,799 B1 | 8/2002 | Cen |
| 6,467,981 B1 | 10/2002 | Gueret |
| 6,491,928 B1* | 12/2002 | Smith, III .................... 424/401 |
| 6,491,937 B1 | 12/2002 | Slavtcheff |
| 6,547,468 B2 | 4/2003 | Gruenbacher |
| 6,550,092 B1 | 4/2003 | Brown |
| 6,607,739 B1 | 8/2003 | Wallo |
| 6,638,527 B2 | 10/2003 | Gott |
| 6,677,294 B2 | 1/2004 | Shaw |
| 6,730,317 B2 | 5/2004 | Gueret |
| 6,783,294 B2 | 8/2004 | Duden |
| 6,835,701 B2 | 12/2004 | Seipel |
| 6,878,380 B2 | 4/2005 | Farrell |
| 6,883,353 B2 | 4/2005 | Goldani |
| 6,902,338 B2 | 6/2005 | Puvvada |
| 6,903,057 B1 | 6/2005 | Tsaur |
| 6,906,016 B1 | 6/2005 | Tsaur |
| 6,977,238 B1 | 12/2005 | Wetzel |
| 7,115,535 B1 | 10/2006 | Smith |
| 7,229,956 B2 | 6/2007 | Bedford |
| 7,381,693 B2 | 6/2008 | Keenan |
| 7,419,321 B2 | 9/2008 | Tereschouk |
| 7,462,348 B2 | 12/2008 | Gruenbacher |
| 7,581,273 B2 | 9/2009 | Dobrin |
| 7,874,756 B2 | 1/2011 | Nuebel |
| 2001/0003565 A1 | 6/2001 | McOsker |
| 2001/0018068 A1 | 8/2001 | Lorenzi |
| 2001/0028894 A1 | 10/2001 | Gueret |
| 2002/0110655 A1 | 8/2002 | Seth |
| 2002/0155281 A1 | 10/2002 | Lang |
| 2002/0192268 A1 | 12/2002 | Alwattari |
| 2003/0079323 A1 | 5/2003 | Ngai |
| 2003/0084914 A1* | 5/2003 | Simon .................... 132/333 |
| 2003/0143263 A1 | 7/2003 | Durden |
| 2003/0180242 A1 | 9/2003 | Eccard |
| 2003/0194425 A1 | 10/2003 | Simon |
| 2003/0228351 A1 | 12/2003 | Hasenoehrl |
| 2003/0228352 A1 | 12/2003 | Hasenoehrl |
| 2004/0005831 A1 | 1/2004 | Gillette |
| 2004/0116017 A1 | 6/2004 | Smith |
| 2004/0126177 A1 | 7/2004 | Puvvada |
| 2004/0147189 A1 | 7/2004 | Smith |
| 2004/0175343 A1 | 9/2004 | Osborne |
| 2004/0176002 A1 | 9/2004 | Siegwart |
| 2004/0237234 A1 | 12/2004 | Young |
| 2004/0237235 A1 | 12/2004 | Visioli |
| 2004/0244132 A1 | 12/2004 | Ouellette |
| 2005/0148260 A1 | 7/2005 | Kopacz |
| 2005/0202068 A1 | 9/2005 | Hasenoehrl |
| 2005/0226834 A1 | 10/2005 | Lambino |
| 2005/0276828 A1 | 12/2005 | Grissett |
| 2005/0277566 A1 | 12/2005 | Grissett |
| 2006/0234894 A1 | 10/2006 | Taylor |
| 2006/0246119 A1 | 11/2006 | Eknoian |
| 2006/0251464 A1 | 11/2006 | Bauer |
| 2006/0281650 A1 | 12/2006 | Keenan |
| 2006/0281651 A1 | 12/2006 | Keenan |
| 2006/0281652 A1 | 12/2006 | Keenan |
| 2007/0045135 A1 | 3/2007 | Berger |
| 2007/0071797 A1 | 3/2007 | Hernandez-Munoa |
| 2007/0099813 A1 | 5/2007 | Luizzi |
| 2007/0130706 A1 | 6/2007 | Buhrow |
| 2007/0130707 A1 | 6/2007 | Cohen |
| 2007/0283516 A1 | 12/2007 | Rasmussen |
| 2008/0075748 A1 | 3/2008 | Hasenoehrl |
| 2008/0104787 A1 | 5/2008 | Keenan |
| 2008/0145388 A1* | 6/2008 | Roreger et al. ............. 424/401 |
| 2008/0168748 A1 | 7/2008 | McCloskey |
| 2008/0247806 A1 | 10/2008 | Todd |
| 2008/0274147 A1 | 11/2008 | Schaeffer et al. |
| 2009/0178692 A1 | 7/2009 | Warr |
| 2009/0180826 A1 | 7/2009 | Guay |
| 2009/0246376 A1 | 10/2009 | Gunn |
| 2010/0074671 A1 | 3/2010 | Prax |
| 2010/0130988 A1 | 5/2010 | Bolton |
| 2011/0278429 A1 | 11/2011 | Jha |
| 2012/0028869 A1 | 2/2012 | Crawford |
| 2012/0246851 A1 | 10/2012 | Smith |

FOREIGN PATENT DOCUMENTS

| | | |
|---|---|---|
| CN | 1046273 | 10/1990 |
| CN | 1117835 | 3/1996 |
| DE | 19744213 | 4/1999 |
| DE | 10208678 | 9/2002 |
| DE | 20304298 | 6/2003 |
| DE | 10301838 | 7/2004 |
| DE | 202004007851 | 8/2004 |
| EP | 0032793 | 7/1981 |
| EP | 0047116 | 3/1982 |
| EP | 0211664 | 2/1987 |
| EP | 0272492 | 6/1988 |
| EP | 0353013 | 1/1990 |
| EP | 0863201 | 9/1998 |
| EP | 1000605 | 5/2000 |
| EP | 1153554 | 11/2001 |
| FR | 2822045 | 9/2002 |
| FR | 2855741 | 12/2004 |
| FR | 2867067 | 9/2005 |
| GB | 2130965 | 6/1984 |
| GB | 2163947 | 3/1986 |
| GB | 2222526 | 3/1990 |
| GB | 2303541 | 2/1997 |
| JP | 61277608 | 12/1986 |

(56) References Cited

FOREIGN PATENT DOCUMENTS

| | | |
|---|---|---|
| JP | 2265516 | 10/1990 |
| JP | 8084684 | 4/1996 |
| JP | 9299271 | 11/1997 |
| JP | 10000170 | 1/1998 |
| JP | 10183194 | 7/1998 |
| JP | 2002142857 | 5/2002 |
| JP | 2002275031 | 9/2002 |
| JP | 2002315689 | 10/2002 |
| JP | 2004016560 | 1/2004 |
| JP | 2004236996 | 8/2004 |
| JP | 2006082263 | 3/2006 |
| JP | 2006130194 | 5/2006 |
| JP | 2009292750 | 12/2009 |
| JP | 2010046129 | 3/2010 |
| WO | WO 9526710 | 10/1995 |
| WO | WO 9827193 | 6/1998 |
| WO | WO 9828399 | 7/1998 |
| WO | WO 9925318 | 5/1999 |
| WO | WO 0108655 | 2/2001 |
| WO | WO 0108658 | 2/2001 |
| WO | WO 02092050 | 11/2002 |
| WO | WO 03053397 | 3/2003 |
| WO | WO 2008113973 | 9/2008 |

OTHER PUBLICATIONS

U.S. Appl. No. 13/585,876, filed Aug. 15, 2012, Smith et al.
U.S. Appl. No. 13/585,881, filed Aug. 15, 2012, Smith et al.
International Search Report and Written Opinion of PCT/US2012/032054 dated Jul. 4, 2012.
International Search Report of PCT/US00/01387 dated Sep. 20, 2000.
Written Opinion of PCT/US00/01387 dated Oct. 20, 2000.
International Search Report and Written Opinion of PCT/US2012/050873 dated Dec. 10, 2012.
International Search Report and Written Opinion of PCT/US2012/050874 dated Dec. 12, 2012.
International Search Report and Written Opinion of PCT/US2012/050877 dated Dec. 6, 2012.

* cited by examiner

PERSONAL CARE ARTICLES HAVING MULTIPLE ZONES WITH COMPLIANT PERSONAL CARE COMPOSITIONS

CROSS REFERENCE TO RELATED APPLICATION

This application claims priority to U.S. Provisional Application Ser. No. 61/523,824 filed Aug. 15, 2011, and hereby incorporates the same provisional application by reference herein in its entirety.

TECHNICAL FIELD

The present disclosure generally relates to personal care articles.

BACKGROUND

Cleansing the skin and/or hair is an activity that has been done for many years. Over time, skin and hair cleansing have involved the use of compositions such as bar and liquid soaps, body washes, shampoos, conditioners, and the like. For these compositions, consumers desire good cleansing properties and lathering characteristics, mildness toward the skin, and the ability to provide benefit agents to the target surface.

To enhance a consumer's experience, such cleansing compositions can also be coupled with implements such as a washcloth, a sponge, or a puff. For example, many consumers dispense liquid soaps or body washes onto a puff and then cleanse by applying the puff to their skin and/or hair. Similarly, many consumers rub bar soaps with a washcloth and then cleanse by applying the washcloth to their skin and/or hair.

Although a consumer's experience with a cleansing composition can be enhanced by coupling the cleansing composition with an implement, to date, such an experience has not been completely ideal. For example, coupling such cleansing compositions with an implement tends to lead to clutter in the shower or bath as a consumer needs to carry or store cumbersome bottles, bars, jars, and/or tubes of cleansing products and implements themselves. Additionally, coupling requires the user to perform additional steps of applying the body wash or soap on the implement and then rubbing or wiping the implement on their skin rather than just applying the body wash and/or soap directly. As such, more water tends to be consumed increasing the waste and carbon footprint of the consumer. And further, certain personal cleansing compositions, such as bar soaps, can have difficulty providing the consumer desired deposition of benefit agents, even when coupled with an implement.

Some attempts have been made to combine an implement with a personal cleansing composition in a personal care article. However, these executions were not ideal. For example, one such article included a rigid bar soap coupled with an implement. The rigidity of this type of execution does not conform to the surface to which it is applied making it difficult to thoroughly clean the target surface. Some other attempts at a more conformable product did not provide a desired reusability and tended to create additional waste. In particular, such cleansing articles tend to lack durability and/or include cleansing compositions that completely dissolve after very few uses.

Accordingly, it would be desirable to provide a personal care article having a compliant personal care composition that can have desirable cleansing properties, including suitable lathering and rinsing characteristics, can conform to the skin and/or hair, can be reusable and easy to use. It would also be desirable to provide a personal care article having multiple zones which can be utilized to enhance a cleansing experience. Further, it would be desirable to provide a method for increasing lather production and other lathering characteristics.

SUMMARY OF THE INVENTION

A personal care article comprises a first compliant personal care composition, a second compliant personal care composition, and a first water penetrable substrate. The first compliant personal care composition is in a first zone. The second compliant personal care composition is in a second zone. Each of the zones is defined by one or more barriers. The first water penetrable substrate is adjacent to the first and second compliant personal care compositions. A total compliant personal care composition is greater than about 3,500 wt. %, by weight of a total substrate.

A personal care article comprises about 4,000 wt. % or more, by weight of a total substrate, of a total compliant personal care composition, a first substrate, and a second substrate. A first compliant personal care composition is in a first zone. A second compliant personal care composition is in a second zone. Each of the zones is defined by one or more barriers. The first and second compliant personal care compositions are configured to be released at each zone. The first substrate surrounds the first and second compliant personal care compositions. The first substrate has a water flux rate of about 0.1 $cm^3/cm^2/s$ to about 60 $cm^3/cm^2/s$. The second substrate surrounds the first substrate. The second substrate has a water flux rate of about 0.1 $cm^3/cm^2/s$ to about 60 $cm^3/cm^2/s$.

DETAILED DESCRIPTION OF THE INVENTION

I. Definitions

Figure 1:
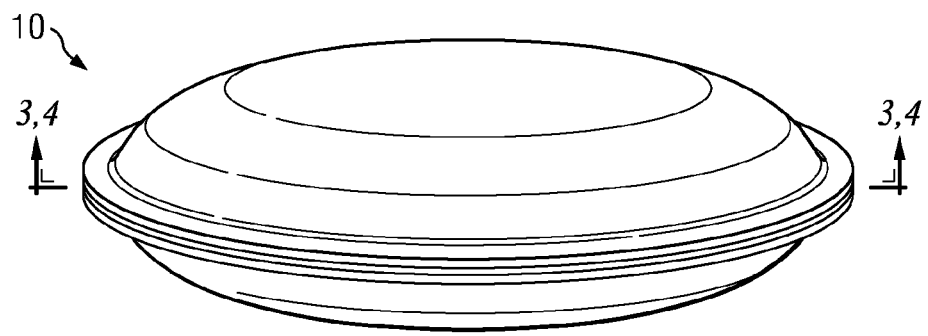
FIG. 1 depicts a perspective view of a personal care article according to one example.

As used herein, the following terms shall have the meaning specified thereafter:

"Cleansing composition" refers to compositions intended for topical application to a surface such as skin and/or hair to remove, for example, dirt, oil, and the like. The cleansing compositions disclosed herein can be rinse-off formulations, in which the composition is applied topically to the skin or hair via, for example, an implement or substrate and then subsequently rinsed within seconds to minutes from the skin and/or hair with water.

"Compliant" as used herein refers to an article and/or composition that can at least partially conform to a surface to which it is applied by some degree of deformation.

"g/use" refers to grams per use, which is the unit used for rate of consumption. The method for measuring and/or calculating the rate of consumption is described herein.

"Macroapertured" refers to a substrate containing well-defined apertures having an average diameter of about 300 microns or greater.

"Microapertured" generally refers to a substrate containing well-defined microscopic apertures (i.e., those not readily visible to a naked eye having 20/20 vision).

"Natural" refers to materials that can be derived from plants, animals, insects, or materials that can be byproducts of plants, animals, and insects.

"Nonwoven" refers to a substrate comprising fibers not woven into a fabric but rather formed into a sheet. The fibers can either be random (i.e., randomly aligned) or the fibers can be non-random. For example, the nonwoven can be carded (i.e., combed to be oriented in primarily one direction).

"Personal care" refers to a composition or article for topical application to skin and/or hair. Personal care compositions can be rinse-off formulations, in which the composition can be applied topically to the skin and/or hair and then subsequently rinsed within seconds to minutes of application. The composition could also be wiped off using a substrate.

"Personal care article" refers to an article that can include a personal care composition and a water penetrable substrate. The personal care article can be reusable.

"Reusable" refers to an article that can be used for a number of usage events, such as showers and/or baths, wherein the number of usage events can be about 5 or greater, about 7 or greater, about 10 or greater, about 15 or greater, about 20 or greater, about 25 or greater, or about 30 or greater.

"Substantially free of refers to about 5% or less, about 3% or less, about 1% or less, or about 0.1% or less of a stated ingredient. "Free of refers to no detectable amount of the stated ingredient or thing.

"Substrate" refers to a material which can limit the amount of water to which a personal care composition is exposed during a usage event versus exposure of a personal care composition itself absent a substrate. The substrate may be, for example, a film, formed film, batting, woven, nonwoven, or a combination thereof.

"Synthetic" refers to materials that can be obtained primarily from various man-made materials or from natural materials which have been altered.

"Usage event" refers to one 5 minute cycle of the Consumption Test below.

"Water insoluble substrate" refers to a substrate which does not dissolve in water during the life of the article.

"Water penetrable substrate" refers to a substrate which provides sufficient water to penetrate the personal care article to provide desired lather capabilities.

II. Personal Care Articles

Personal care articles can come in many forms. One of the more common forms is bar soap. Bar soap can be generally non-compliant and rigid. The rigidity of most bar soaps can make them difficult to grip, making it more difficult to use during cleansing. Rigid bar soaps can also have the disadvantage in that only the surface which directly contacts the skin can be used for cleansing, and surface area can be limited by the bar's non-compliant nature. Conventional rigid bar soap can have a compliance value of about 2.5 kg/mm or above.

Insoluble components in bar compositions can contribute to bar rigidity. Utilizing compliant articles and/or compositions can forgo a need for rigidity and can often result in elimination of the insoluble components giving a faster dissolving composition. And while it is desirable to have a composition that provides sufficient cleaning properties during a cleansing event (i.e., dissolves well enough to release surfactant), there should be a balance between such cleaning properties and longevity of the composition. Otherwise, the personal care composition can be entirely consumed in just one or a few events and the composition can be too expensive and wasteful to the environment.

How quickly an article or composition is used up by a consumer can be measured by its consumption rate, the method of which is described below. Substrates can be used to control the rate of consumption. So, when compositions dissolve quickly, substrates can be used to increase the consumption rate to a desirable level, like that of a typical bar soap. In certain examples, a substrate can act as a water flux limiting substrate to effectively increase the consumption rate. In certain examples, the water flux of the substrate can be manipulated by the chemical or physical make-up of the substrate. For example, the substrate can contain pores to allow more water passage. If less water passage is desired, the pore number can be reduced during manufacturing of the substrate or some of the pores can be sealed off.

A personal care article can include a substrate and a personal care composition. The personal care article may also comprise multiple substrates and/or multiple personal care compositions. The personal care article may be used, for example, for cleansing of skin, cleansing of hair, shave preparation, post-shave treatment, or a combination thereof. In one example, the personal care article is a personal cleansing article. In certain examples, the personal care article can be reusable.

A personal care composition can have compliant characteristics. For example, if the personal care composition is a compliant personal cleansing composition for cleansing the skin, then the composition will bend to some degree to more fully contact a curved portion of the body, such as an arm. Thus, if the compliant personal cleansing composition is originally flat with no curve, when applied to an arm for cleansing there would be some amount of bend to better conform to the arm. Likewise, if the composition's shape has a small amount of a curve, when applied to the arm the composition would bend to some degree to more fully contact the arm. Oppositely, if the original personal care composition is curved such that it would not need to bend to conform to a curved surface like the arm, then it would bend to straighten when applied to a less curved surface like an abdomen.

In certain examples, compliance of a personal care composition can be measured according to the Compliance Test described in more detail below. In certain examples, a personal care composition can comprise a compliance value of about 1.50 kg/mm or less. In certain examples, the compliance value of the personal care composition can be about 1.35 kg/mm or less; about 1.25 kg/mm or less; about 1.2 kg/mm or less; about 1.1 kg/mm or less; or about 1.0 kg/mm or less. In certain examples, the personal care composition can have a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; and/or about 0.10 kg/mm to about 1.1 kg/mm.

In some examples, the article and/or composition can become compliant after exposure to water. Thus, you may have a non-compliant article or composition that, after exposure to a liquid, like water, during a usage event, becomes compliant. If an article or composition becomes compliant by the end of a second usage event, then it is considered compliant.

A personal care article can have a rate of consumption. Rate of consumption is a measure of how much of the composition is used during a usage event. A method for measuring consumption rate of the article is described in more detail below. In one example, a personal care article can have a consumption rate of about 20 g/use or less. In certain examples, a personal care article can have a consumption rate of about 15 g/use or less. In certain examples, a personal care article can have a consumption rate of about 1.5 g/use to about 15 g/use; from about 2.5 g/use to about 10 g/use; and/or from about 3.5 g/use to about 6.5 g/use.

Figure 2:
FIG. 2 depicts a side view of the personal care article of FIG. 1.
Figure 3:
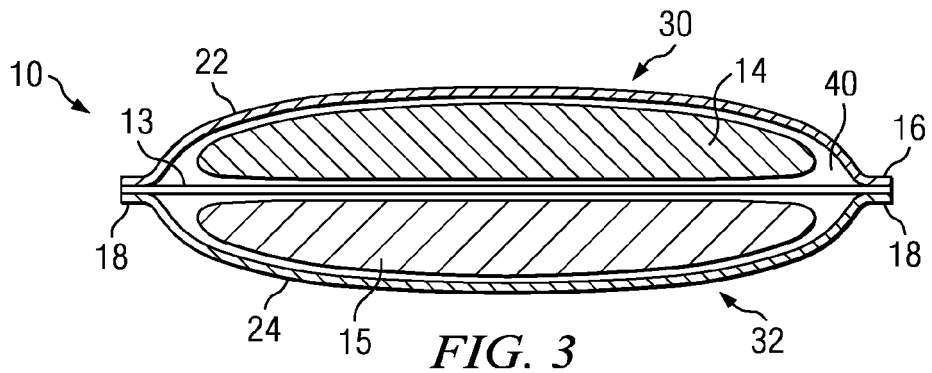
FIG. 3 depicts a cross-sectional view of the personal care article of FIG. 1, along line 3-3.

In certain examples, a personal care article can comprise a compliant personal care composition and a first water penetrable substrate. A personal care article 10 according to one example is shown in FIGS. 1-3, respectively. As more clearly illustrated in FIG. 3, the personal care article 10 can include a first compliant personal care composition 14 and a second compliant personal care composition 15. The first water penetrable substrate 22 can be adjacent to the first compliant personal care composition 14, and a second water penetrable substrate 24 can be adjacent to the second compliant personal care composition 15 as further shown in FIG. 3. A barrier 13 defines a first zone 30 and a second zone 32 such that the first compliant personal care composition 14 is substantially positioned at the first zone 30 and the second compliant personal care composition 15 is substantially positioned at the second zone 32. In one example depicted in FIG. 3, a seal 16 joining the first and second water penetrable substrates (22, 24) is only visible on the ends 18, but can surround the first and second compliant personal care compositions (14, 15). The first and second water penetrable substrates (22, 24), however, can be sealed in other configurations or only partially sealed so as to form, for example, a pouch. The first and second water penetrable substrates (22, 24) can be formed of the same or different materials.

In certain examples, a personal care article can comprise first and second compliant personal care compositions, which can be in first and second zones, and a first water penetrable substrate. The first and second zones can be defined by one or more barriers. In certain examples, the first compliant personal care composition can be the same as the second compliant personal care composition. However, in certain examples, a personal care article can comprise two or more personal care compositions, where each of the personal care compositions can be in two or more zones. In certain examples, the personal care article can further comprise a third compliant personal care composition in a third zone, where each of the first, second, and third zones is defined by one or more barriers, and where the first water penetrable substrate is adjacent to the first, second, and third compliant personal care compositions; in other examples, the personal care article can further comprise a fourth compliant personal care composition in a fourth zone, where each of the first, second, third, and fourth zones is defined by one or more barriers, and where the first water penetrable substrate is adjacent to the first, second, third, and fourth compliant personal care compositions; in other examples, the personal care article can further comprise a fifth compliant personal care composition in a fifth zone, where each of the first, second, third, fourth, and fifth zones is defined by one or more barriers, and where the first water penetrable substrate is adjacent to the first, second, third, fourth, fifth compliant personal care compositions; and so on. Each of the compliant personal care compositions can be configured to be released at the respective zones.

A compliant personal care composition can be a rinse-off composition (e.g., a cleanser) or a leave-on composition (e.g., a moisturizer). In certain examples, a personal care composition can comprise a cleansing phase, and in certain examples, the personal care composition can comprise a benefit phase. In certain examples, a personal care composition can comprise a cleansing phase and a benefit phase, where the cleansing phase can be a continuous phase domain. The personal care composition can further comprise one or more benefit agents that can be deposited to the skin and/or hair of an individual. The cleansing phase and benefit phase can be included in one or more zones such that deposition of a benefit agent can occur during cleansing. In an example having a first zone and a second zone, one of the first zone and the second zone can be a cleansing phase and a benefit phase, wherein the cleansing phase and the benefit phase can be blended. In another such example, one of the first zone and the second zone can be a cleansing phase and a benefit phase, wherein the cleansing phase and the benefit phase can be patterned.

In certain examples, deposition of a benefit agent can occur after cleansing. In an example having a first zone and a second zone, one of the first zone and the second zone can be a cleansing phase and the other can be a benefit phase, which can be used after cleansing to apply a benefit agent to the skin of an individual. Such an arrangement can allow an individual to cleanse the skin and/or hair prior to applying the benefit agent via the zone having the benefit phase.

Figure 4:
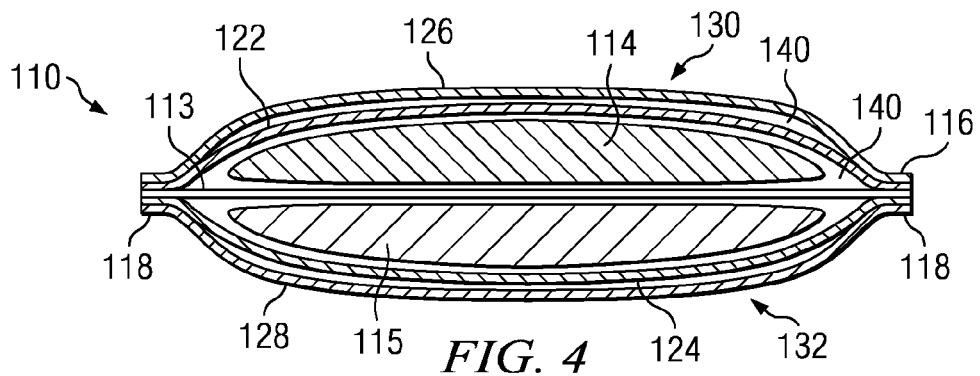
FIG. 4 depicts a cross-sectional view of another example of a personal care article of FIG. 1, along line 4-4, where additional substrates have been added.

In another example, as illustrated in FIG. 4, a personal care article 110 can include a first compliant personal care composition 114 and a second compliant personal care composition 115. A first water penetrable substrate 122 can be adjacent to the first compliant personal care composition 114, while a second water penetrable substrate 124 can be adjacent to the second compliant personal care composition 115. And similar to the personal care article shown in FIG. 3, a barrier 113 can define a first zone 130 and a second zone 132 such that the first compliant personal care composition 114 is located at the first zone 130 and the second compliant personal care composition 115 is located at the second zone 132. As illustrated in FIG. 4, a seal 116 joining the first and second water penetrable substrates (122, 124) can be only visible on the ends 118, but can surround the first and second compliant personal care compositions (114, 115). In addition, a first water insoluble substrate 126 can be adjacent to the first water penetrable substrate 122 and a second water insoluble substrate 128 can be adjacent to the second water penetrable substrate 124. The first and second water insoluble substrates (126, 128) may be formed from the same or different materials. Like the seal of the first and second water penetrable substrate (122, 124), while only visible on the ends 118, the seal 116 of the first and second water insoluble substrates (126, 128) can surround the first and second compliant personal care compositions (114, 115). The seal 116 of the first and second water insoluble substrate (126, 128) may, however, be sealed in other configurations, or, may only be partially sealed so as to form, for example, a pouch.

The personal care article may also comprise a chamber 40, 140, as seen, for example, in FIGS. 3-4. In certain examples, a chamber can be a space between a substrate and a personal care composition or between a substrate and another substrate, where the substrate is not touching the personal care composition or the other substrate. The substrate(s) can be flexible such that they touch the personal care composition (or another substrate) in some areas and not others. The locations where the substrate can be touching or not touching the personal care composition or other substrate can move as the substrate(s) and personal care composition shift during handling and/or use.

Figure 5A:
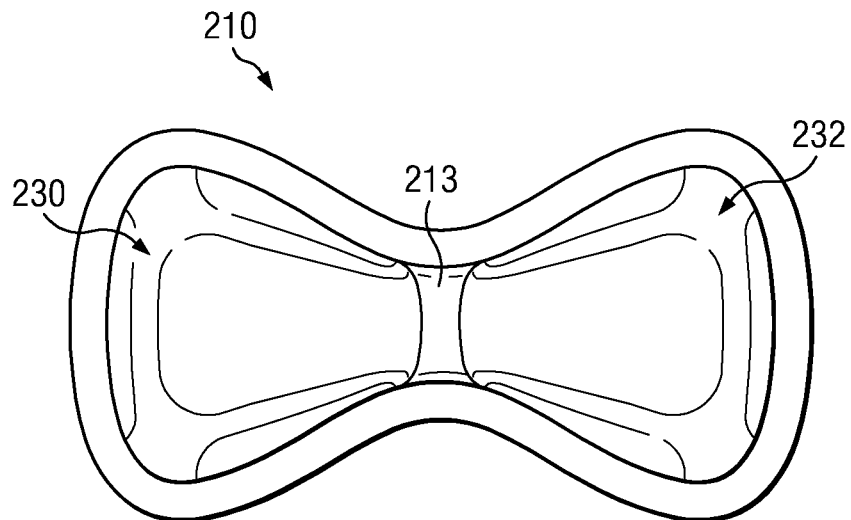
FIG. 5A depicts a top view of a personal care article according to another example.
Figure 5B:
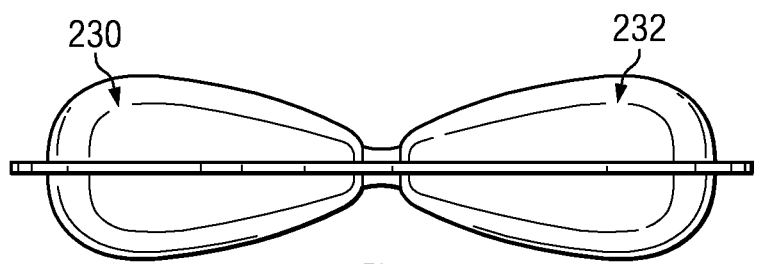
FIG. 5B depicts a side view of the personal care article of FIG. 5A.
Figure 5C:
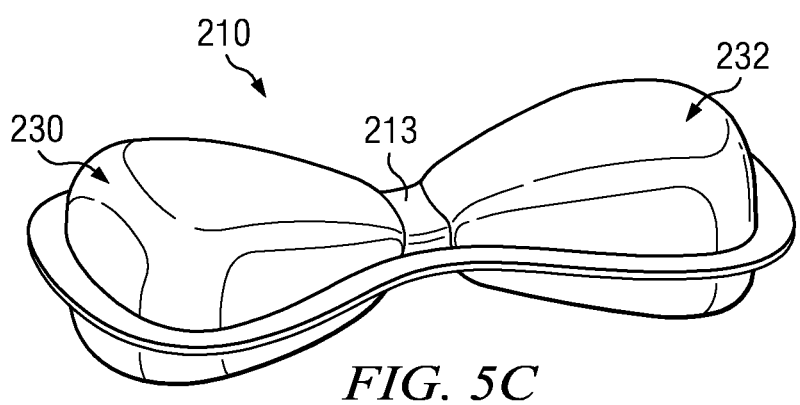
FIG. 5C depicts a perspective view of the personal care article of FIG. 5A.
Figure 6A:
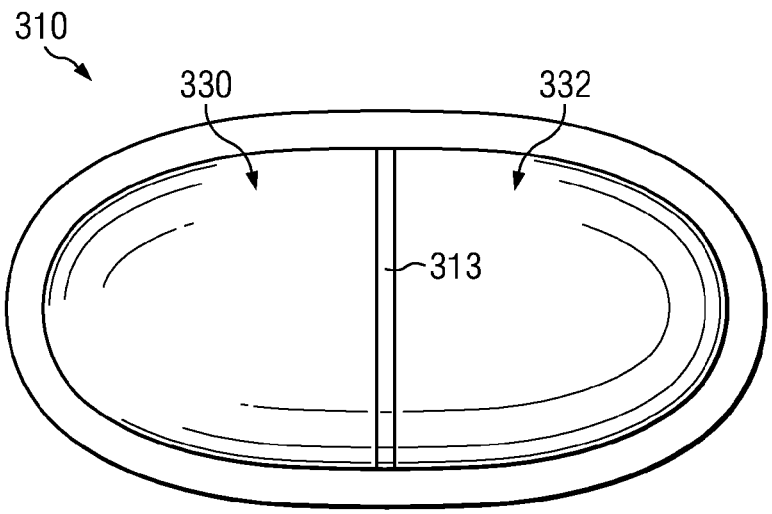
FIG. 6A depicts a top view of a personal care article according to another example.
Figure 6B:
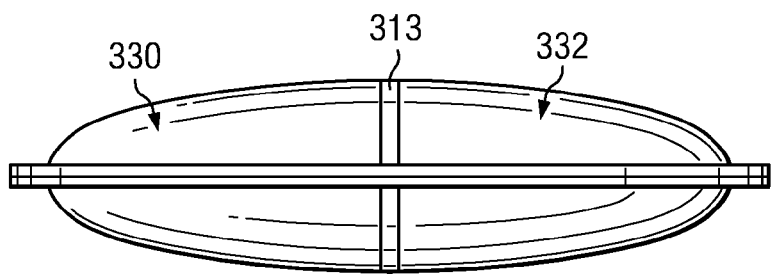
FIG. 6B depicts a side view of the personal care article of FIG. 6A.
Figure 6C:
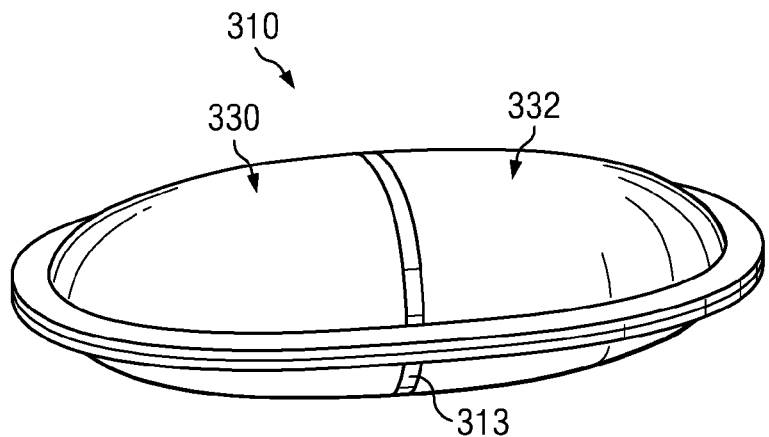
FIG. 6C depicts a perspective view of the personal care article of FIG. 6A.

As noted above, personal care articles can have a variety of configurations. In one such configuration, a personal care article can include a top side and a bottom side. As in the examples depicted in FIGS. 3-4, a first zone can be on a top side of the personal care article and a second zone can be on a bottom side of the personal care article. However, in other examples, the first zone can be on the bottom side and the second zone can be on the top side. Further, in certain examples, the personal care article can have a configuration which includes having a right side and a left side, and the first zone can be located at one of either the right side or the left side and the second zone can be located at the remaining side. In one such example, as shown in FIGS. 5A, 5B, and 5C, a first zone 230 is shown to be located on a left side and a second zone 232 is located on a right side, where the first zone 230 and the second zone 232 are defined by a barrier 213. In such an example, both the first zone 230 and the second zone 232 can be positioned to simultaneously contact the skin and/or hair of an individual upon application of the personal care article 210. In another example, and as shown in FIGS. 6A, 6B, and 6C, first and second zones 330, 332 can take different shapes than those shown in FIGS. 5A, 5B, and 5C, but a personal care article 310 can still take a similar configuration as that shown in FIGS. 5A, 5B, and 5C, such that a first zone 330 is shown to be located on a left side and a second zone 332 is located on a right side, the first zone 330 and the second zone 332 are defined by a barrier 313, and both the first zone 330 and the second zone 332 can be positioned to simultaneously contact the skin and/or hair of an individual upon application of the personal care article 310. In certain examples, one of the top side and the bottom side can be a cleansing composition with a benefit phase. Similarly, in other examples, one of the right side and the left side can be a cleansing composition with a benefit phase.

Figure 7:
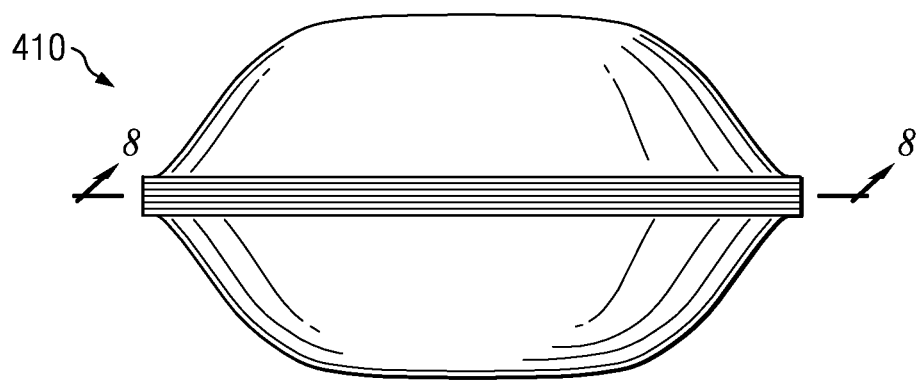
FIG. 7 depicts a side view of a personal care article according to another example.
Figure 8:
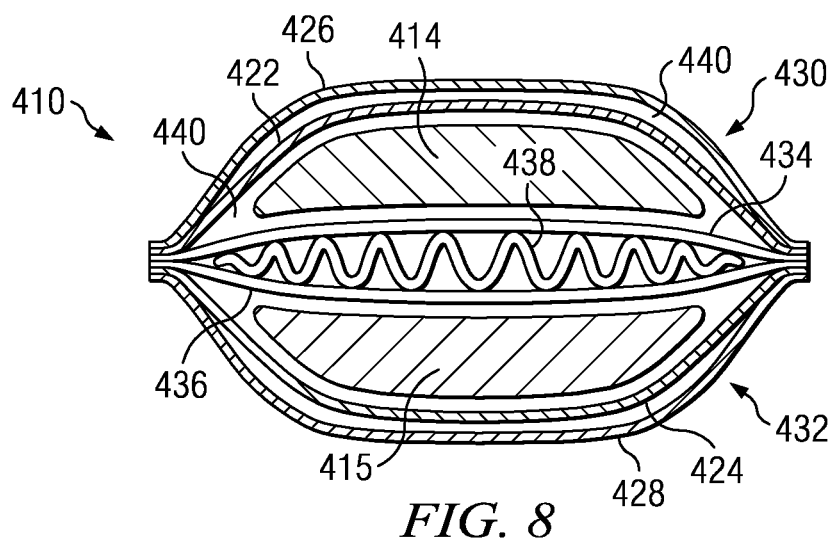
FIG. 8 depicts a cross-sectional view of the personal care article of FIG. 7, along line 8-8.

A personal care article according to other certain examples is shown in FIGS. 7-8. The personal care article 410 can include a first compliant personal care composition 414 in a first zone 430 and a second compliant personal care composition 415 in a second zone 432. A first water penetrable substrate 422 can be adjacent to the first compliant personal care composition 414 in the first zone 430, while a second water penetrable substrate 424 can be adjacent to the second compliant personal care composition 415 in the second zone 432. The first compliant personal care composition 414 and the second compliant personal care composition 415 can be separated by a first interior substrate 434, a second interior substrate 436, and/or a first barrier 438. In particular, the first interior substrate 434 can be positioned between the first barrier 438 and the first zone 430 and the second interior substrate 436 can be positioned between the first barrier 438 and the second zone 432. In addition, a first water insoluble substrate 426 can be adjacent to the first water penetrable substrate 422 and a second water insoluble substrate 428 can be adjacent to the second water penetrable substrate 424. The first and second water insoluble substrates (426, 428) can be formed of the same or different material. In certain examples, a first compliant personal care composition can be the same as a second compliant personal care composition. As described herein, a chamber 440 can be a space between a substrate and a personal care composition or between a substrate and another substrate, where the substrate is not touching the personal care composition or the other substrate. In certain examples, a first barrier can be a bunched substrate, nonwoven (i.e., a natural or synthetic nonwoven including fibrous and nonfibrous nonwovens), a woven, a film (e.g., a formed film), a sponge (e.g., a natural and/or synthetic sponge), a polymeric netted mesh (i.e., a "scrim"), a batting, spunbound, spunlace, hydroentangled, carded, needlepunch, or any other suitable material as described below in more detail, such that the first barrier can act as a spring or pump to facilitate agitation of the personal care article and increase lather production. In certain examples, a first barrier can avoid interfering with sealing of first and second water penetrable substrates and/or first and second water insoluble substrates, such that a seal can exclude the first barrier.

The personal care article can include from about 0.5% to about 25,000%, by weight of a total substrate(s), of a total compliant personal care composition, which can be a combination of all personal care compositions (e.g., first compliant personal care composition, second compliant personal care composition) in a personal care article. The total substrate can be a combination of all substrates in a personal care article. For example, a personal care article can include greater than about 3,500%, by weight of the total substrate(s); greater than about 4,000%, by weight of the total substrate(s); greater than about 4,250%, by weight of the total substrate(s); greater than about 4,500%, by weight of the total substrate(s); greater than about 4,750%, by weight of the total substrate(s); greater than about 5,000%, by weight of the total substrate(s), of a total compliant personal care composition; or any combination thereof.

Personal care articles can have any suitable shape, for example, oval, square, rectangular, circular, triangular, hour glass, hexagonal, c-shaped, etc.

Without wishing to be bound by theory, and as set forth above, it is believed that a personal care article can eliminate problems associated with reusability, waste, consumption, lather, dissolution, and conformity or compliancy. As described herein, it has been found that use of a personal care composition can improve longevity of a personal care article such that the personal care article can be used for a number of usage events and can conform to or mimic a shape of the surface to which the personal care composition is applied. Further, it has been found that such a personal care composition can be combined with a water insoluble substrate made of particular materials to control water flux and, thus, dissolution and consumption of the personal care composition to increase the longevity of the personal care article without sacrificing lather or other properties desirable to consumers thereof A cleansing experience can be enhanced by providing a personal care article having multiple zones. As personal care regimens can include compositions for cleansing the skin and/or hair, compositions for delivering one or more benefit agents to the skin and/or hair, and compositions that are capable of both, several personal care composition containers and/or personal care articles comprising such personal care compositions, and thus, extra steps, can be required to provide both desired cleansing and benefit properties. As such, consumers can be discouraged from purchasing and/or using multiple personal care compositions and forgo obtaining such desired cleansing and benefit properties to avoid resulting shower clutter, additional and/or elaborate steps, or additional expenses associated with multiple containers and articles.

Without wishing to be bound by theory, it is believed that providing a personal care article having multiple zones can eliminate problems associated with efficiency, ergonomics, and waste. A personal care article can include a cleansing phase and a benefit phase such that distribution of cleansing and benefit properties can be controlled. In certain examples, one zone can include both a cleansing phase and a benefit phase, and in other examples, one zone can be a cleansing phase and the other can be a benefit phase. For example, different zones can be applied simultaneously or in series, and one or more benefit agents can be deposited to the skin and/or hair of an individual from a cleansing phase and/or a benefit phase. By including multiple zones in a single personal care article, steps involving multiple containers and/or articles can be eliminated and consumers can benefit from ease of using a singular personal care article to obtain desired cleansing and benefit properties.

Methods for increasing lather properties can include providing a personal care article having two or more zones defined by one or more barriers. Lather can be produced in a personal care article having personal care compositions by manually agitating the personal care article. However, by increasing aeration in the personal care article, lather produced by such agitation can be improved.

Without wishing to be bound by theory, it is believed that by providing one or more barriers between zones, additional oxygen can be introduced to the personal care compositions during agitation to increase the lather produced, and thus, the personal care article can be used more efficiently and effectively.

A. Substrates

A personal care article can comprise at least one substrate. The substrate can enhance cleansing and therapeutic treatment of a surface such as skin and/or hair. For example, by physically coming into contact with the skin and/or hair, the substrate can aid in the cleansing and removal of dirt, makeup, dead skin, and other debris such that the substrate can act as an efficient lathering and/or exfoliating implement but can also be non-abrasive to the skin. A substrate can be a composite (i.e., there are multiple plies to the substrate which may be of the same or different materials). In one example, the substrate can be water insoluble. In other examples, the substrate can be water penetrable. However, in certain examples, the personal care article can comprise both water penetrable substrates and water insoluble substrates.

In certain examples, a substrate can at least partially surround one or more personal care compositions. In other examples, a substrate can entirely surround one or more personal care compositions. A substrate can be in the form of a pouch, pocket, wrap, or any other suitable configuration to maintain one or more personal care compositions.

As set forth above, the substrate can be water penetrable. Where the substrate is water penetrable, the substrate can have a water flux rate. The water flux rate can be used to limit wetting of the personal care composition included in the personal care article, thereby controlling lather, dissolution, and/or consumption of the composition included in the personal care article. Without being limited by theory, the first substrate can manage or limit the water flux rate to provide controlled wetting and to extend a useful life of a personal care composition while still enabling enough wetting to provide, for example, suitable lather. In certain examples, the water flux rate can be from about $0.1$ $cm^3/cm^2/s$ to about $200$ $cm^3/cm^2/s$, from about $0.4$ $cm^3/cm^2/s$ to about $120$ $cm^3/cm^2/s$, from about $20$ $cm^3/cm^2/s$ to about $100$ $cm^3/cm^2/s$, or any combination thereof, as measured by the Water Flux Rate Test disclosed below. The ability to control the water flux rate can allow for adjustment such that the personal care composition, such as a cleansing composition, can be reused and, thus, last through a number of shower, bathing or cleansing experiences while still exhibiting lathering characteristics expected by consumers. In certain examples, there can be a water flux differential between substrates. In certain examples, the flux differential between substrates can be at least about $2.5$ $cm^3/cm^2/s$; about $3.0$ $cm^3/cm^2/s$ or more; or about $4.0$ $cm^3/cm^2/s$ or more.

In certain examples, the substrate can be a nonwoven (i.e., a natural or synthetic nonwoven including fibrous and nonfibrous nonwovens), which can typically have land regions (i.e., regions that do not allow water and/or personal care composition to pass through) and openings; a woven; a film (e.g., a formed film); a sponge, which can include a natural and/or synthetic sponge (e.g., polymeric mesh sponge), examples of which can include those described in European Patent Application No. EP 702550A1 published Mar. 27, 1996; a polymeric netted mesh (i.e., a "scrim"), examples of which can include those described in U.S. Pat. No. 4,636,419; a batting; spunbond; spunlace; hydroentangled; carded; needlepunch; or any other suitable material. In certain examples, the substrate can be a composite material that can include, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. Suitable examples for each type of substrate and other suitable substrate materials are described in U.S. Provisional Application Ser. No. 61/523,824 and U.S. patent application Ser. No. 13/438,918, both of which are incorporated herein by reference.

Parameters to consider when selecting substrates (e.g., formed films) can include thickness, pattern, polymer stiffness, and permeability. Additional information on such parameters is also described in U.S. Provisional Application Ser. No. 61/523,824 and U.S. patent application Ser. No. 13/438,918.

A substrate can include one or more openings such that water, the personal care composition, and/or lather, for example, can pass through the substrate. In one example, where a permeable substrate can be adjacent to the personal care composition, water can pass through the water permeable substrate to interact with the personal care composition. As the personal care composition dissolves, it can then also pass through the substrate to be delivered to a target surface (e.g., skin).

In one example, permeability of openings can be selected based on a dissolution half-life of a personal care composition and a desired reusability of the article. For example, when the dissolution half-life of the personal care composition is high, a higher level of permeability can be selected to counteract the high dissolution half-life and provide a desirable consumption rate for the article. Alternatively, when the dissolution half-life of the personal care composition is low, the permeability of the one or more openings or can be lower and still provide a desirable consumption rate for the article. In certain examples, a substrate can include a permeability of about 1 opening/cm$^2$ or greater, about 10 openings/cm$^2$ or greater, about 100 openings/cm$^2$ or greater, about 500 openings/cm$^2$ or greater, about 1,000 openings/cm$^2$ or greater, about 1,500 openings/cm$^2$ or greater, or any combination thereof.

The openings can be apertured, nonapertured, or a combination thereof. For example, the one or more openings can include well-defined apertures such as microapertures or macroapertures, holes, perforations, cavities, raised or depressed fibrous and/or nonfibrous regions, gaps between regions, and the like that can enable, for example, water and/or the personal care composition to pass through the substrate.

A substrate can be a contact substrate, which can be a substrate for contacting a target surface (e.g., skin). A substrate can also be a noncontact substrate. Noncontact substrates, for example, can be used to help give a personal care article a desired consumption rate, softness, lather properties, etc.

In certain examples, a substrate can require a sufficient tensile strength in order to effectively fulfill a desired role. For example, a contact substrate can require a higher tensile strength than a noncontact substrate because the contact substrate can be in contact with a target surface. In one example, a substrate can provide an ultimate tensile strength of about 10 g/mm width or greater, about 30 g/mm (width) or greater, about 60 g/mm (width) or greater, or about 200 g/mm (width) or greater and a stiffness of about 1 g/mm (width) or greater, about 2 g/mm (width) or greater, about 7 g/mm (width) or greater, about 20 g/mm (width) or greater, or about 80 g/mm (width) or greater, as measured by the Tensile Test described below.

A substrate can further provide a variety of textures. Texturized substrates can be used for both contact and noncontact substrates. In certain examples, the article can have a different texture on each side thereof. For example, the article can include a gripping side and a substrate application side. In one example, the gripping side can include a texture that is the same as the substrate application side. In another example, the gripping side can include a texture that is different than the substrate application side.

In one example, a personal care article can comprise more than one substrate. In one example, a personal care article can comprise more than one contact substrate. A combination of contact substrates can be used, for example, to give different properties to different sides of an article. In one example, a first water insoluble substrate can be a contact substrate which can help gripping and a second water insoluble substrate can be a contact substrate on another portion of the article selected for its application properties. In one example, the personal care article can have an exfoliating contact substrate on one side of the personal care article and a soothing contact substrate on the other side.

A personal care article can include more than one substrate where one substrate can include a contact substrate and another substrate can include a noncontact substrate. In one example, the first and second water insoluble substrates can both be contact substrates, while the first and second water penetrable substrates can both be noncontact substrates. In one example, a noncontact substrate can be at least partially surrounded by at least one contact substrate. In one example, two noncontact substrates can be surrounded by two contact substrates. Further, a personal care article can comprise a first side and a second side, such that the first water penetrable substrate can be adjacent to a first compliant personal care composition on one side of the personal care article, a second water penetrable substrate can be adjacent to a second compliant personal care composition on the other side of the personal care article, a first water insoluble substrate can be adjacent to the first water penetrable substrate, and a second water insoluble substrate can be adjacent to the second water penetrable substrate. Additional contact and non-contact substrates can also surround other substrates and/or a personal care composition.

As set forth above, one or more barriers can define two or more zones of a personal care article. In certain examples, such as the example shown in FIG. 8, a personal care article can include a first zone and a second zone separated by a first interior substrate, a second interior substrate, and a first barrier, such that the first interior substrate can be positioned between the first barrier and the first zone and the second interior substrate can be positioned between the first barrier and the second zone. A barrier can be a substrate, and as such, the barrier can be any of the substrates described herein. In one example, the barrier can be a formed film, a polyurethane sponge, a scrim, a seal, a substrate, or combinations thereof. In certain examples, the barrier can act as a spring or pump to facilitate agitation of the personal care article and increase lather production. In such examples, the barrier can comprise a bunched substrate. In certain examples, the one or more barriers can be substantially impermeable, while in other examples, the barrier can be substantially permeable (e.g., where both the first and second zones comprise a cleansing composition).

A combination of substrates can be used to not only give different user experience properties, like exfoliating versus soothing, but the combination of substrates can also be used to give other desirable properties of a personal care article, such as appropriate consumption rate and lathering properties. When combining substrates to form an article, one should consider the properties of the personal care composition, in addition to individual properties of the substrates, to come up with the personal care article with the desired properties. In one example, first and second compliant personal care compositions can be surrounded by two noncontact substrates which can be surrounded by two contact substrates. In certain examples, the two noncontact substrates can be the same. In certain examples, the two contact substrates can be the same. Further, and as described herein, to provide a desirable consumption rate for a personal care article, a substrate having a higher level of permeability can be selected to counteract a personal care composition having a high dissolution half-life and a substrate having a lower level of permeability can be selected to counteract a personal care composition having a low dissolution half-life. Thus, in certain examples, different substrates can be selected for each zone such that different zones can have similar consumption rates and the personal care article, as a whole, can be consumed at an effective rate.

B. Personal Care Compositions

A personal care article can comprise a substrate and compliant personal care compositions. Such personal care compositions can be rinse-off compositions (e.g., a cleanser) or leave-on compositions (e.g., a moisturizer).

As set forth above, in certain examples, the personal care article can comprise first and second compliant personal care compositions, which can be in first and second zones, and a first water penetrable substrate. The first and second zones can be defined by one or more barriers. In certain examples, the first compliant personal care composition can be the same as the second compliant personal care composition. However, in certain examples, a personal care article can comprise two or more personal care compositions, where each of the personal care compositions can be in two or more zones.

A personal care article may further comprise a third compliant personal care composition in a third zone, where each of the first, second, and third zones is defined by one or more barriers, and where the first water penetrable substrate is adjacent to the first, second, and third compliant personal care compositions; in other examples, the personal care article can further comprise a fourth compliant personal care composition in a fourth zone, where each of the first, second, third, and fourth zones is defined by one or more barriers, and where the first water penetrable substrate is adjacent to the first, second, third, and fourth compliant personal care compositions; in other examples, the personal care article can further comprise a fifth compliant personal care composition in a fifth zone, where each of the first, second, third, fourth, and fifth zones is defined by one or more barriers, and where the first water penetrable substrate is adjacent to the first, second, third, fourth, fifth compliant personal care compositions; and so on. Each of the compliant personal care compositions can be configured to be released at the respective zones.

As described herein, a compliant personal care composition can be a rinse-off composition (e.g., a cleanser) or a leave-on composition (e.g., a moisturizer). In certain examples, a personal care composition can comprise a cleansing phase, and in certain examples, the personal care composition can comprise a benefit phase. In certain examples, a personal care composition can comprise a cleansing phase and a benefit phase, where the cleansing phase can be a continuous phase domain. The personal care composition can further comprise one or more benefit agents that can be deposited to the skin and/or hair of an individual. The cleansing phase and benefit phase can be included in one or more zones such that deposition of a benefit agent can occur during cleansing. In an example having a first zone and a second zone, one of the first zone and the second zone can be a cleansing phase and a benefit phase, wherein the cleansing phase and the benefit phase can be blended. In another such example, one of the first zone and the second zone can be a cleansing phase and a benefit phase, wherein the cleansing phase and the benefit phase can be patterned.

In certain examples, deposition of a benefit agent can occur after cleansing. In an example having a first zone and a second zone, one of the first zone and the second zone can be a cleansing phase and the other can be a benefit phase, which can be used after cleansing to apply a benefit agent to the skin of an individual. Such an arrangement can allow an individual to cleanse the skin and/or hair prior to applying the benefit agent via the zone having the benefit phase.

In certain examples, a personal care composition can have a dissolution half-life. In certain examples, a personal care composition can have a dissolution half-life of from about 1.0 min. to about 15 min.; from about 1.1 min. to about 13 min.; from about 1.2 min. to about 12 min.; from about 1.3 min. to about 11 min.; from about 1.4 min. to about 8.0 min.; from about 1.5 min. to about 5 min.; or any combination thereof, as measured by the Dissolution Rate Test disclosed below.

A personal care composition can be adjacent to one or more substrates. For example, a personal care article can include a personal care composition disposed between the one or more substrates. For example, as shown in FIG. 3, a first compliant personal care composition 14 can be disposed within and adjacent to a first water penetrable substrate 22, and a second compliant personal care composition 15 can be disposed within and adjacent to a second water penetrable substrate 24, with the first compliant personal care composition 14 and the second compliant personal care composition 15 separated by a barrier 13. In one example, a substrate can comprise a compartment (e.g., pouch) that can be filled with a cleansing composition. As described above, the substrate can activate and/or engage the cleansing composition.

A personal care composition can be, for example, a cleansing composition, a moisturizing composition, a pre-shave composition, a post-shave composition, a shampoo, a conditioner, or a combination thereof. In one example, the personal care composition can include a personal cleansing composition. Further, a personal care composition can be in any suitable form. For example, the personal care composition can be in the form of a bar, paste, gel, pellets, beads, or a combination thereof. Additionally, the composition can be of any shape desirable to a user.

In certain examples, a cleansing composition can include a synthetic surfactant, a soap, or a combination thereof. In one example, a cleansing composition can include from about 1% to about 99.5%, from about 5% to about 85%, or from about 10% to about 70%, by weight of the cleansing composition, of a surfactant or a mixture of surfactants. Suitable synthetic surfactants for a personal cleansing composition can include, anionic (e.g., linear and/or branched anionic surfactants), nonionic, cationic, zwitterionic, amphoteric surfactants, soap, or combinations thereof. Preferably the surfactant can be supplied as a high concentration raw material that typically includes greater than about 40% more preferably greater than about 60% of surfactant component of interest in the raw material. Suitable examples can include, sodium laureth sulfate, sodium trideceth sulfate, sodium cocoyl isethionate, linear alkylbenzene sulfonate, cocamide MEA. In certain examples, a cleansing composition can be a soap-based cleansing composition that can include a combination of a soap or a mixture of soaps suitable for application to a substrate and a humectant (e.g., glycerin) or a mixture of humectants. In certain examples, a cleansing composition can typically include from about 40% to about 99.5%, from about 45% to about 75%, or from about 50% to about 65%, by weight of the cleansing composition, of a soap. Suitable examples for each of the above types of surfactants and others, suitable examples of soaps, and soap manufacturing processes are described in U.S. Provisional Application Ser. No. 61/523,824; U.S. Provisional Application Ser. No. 61/620,213; and U.S. patent application Ser. No. 13/438,918, all of which are incorporated herein by reference.

In certain examples, the cleansing composition can include one or more of the following: humectants (e.g., glycerin), which can maintain or provide a particular rheology or viscosity for the cleansing composition such that the cleansing composition can be manipulated to conform to or mimic the surface of the substrate to which the personal care article is being applied; rheology modifiers (e.g., clays, starches, cellulosics), which can maintain or provide a particular rheology or viscosity for the cleansing composition; and polymers (e.g., hydrophobically modified polymers, cationic polymers, deposition polymers), which can structure the cleansing composition, modify the rheology of the cleansing composition, and improve lather, skin feel, and/or deposition of benefit agents. In one example, the cleansing composition can optionally include from about 0.01% to about 20%, from about 0.01% to about 10%, from about 0.1% to about 8%, or from about 0.1% to about 5%, by weight of the cleansing composition, of a hydrophobically modified polymer. In certain examples, the cleansing composition can include from about 10% to about 20%, by weight of the cleansing composition, of a water soluble polymer (e.g., polyvinyl alcohol). Suitable examples of humectants, rheology modifiers, and polymers are also described in U.S. Provisional Application Ser. No. 61/523,824 and U.S. patent application Ser. No. 13/438,918, both of which are incorporated herein by reference.

Optional ingredients can include gums, block copolymers (e.g., Pluronics®), inorganic salts, brighteners, silica, moisturizers, and emulsifiers. Suitable examples of gums, block copolymers, inorganic salts, brighteners, silica, moisturizers, and emulsifiers and other optional ingredients that can be included in a cleansing composition are also described in U.S. Provisional Application Ser. No. 61/523,824 and U.S. patent application Ser. No. 13/438,918, both of which are incorporated herein by reference.

A personal care composition can include one or more benefit agents or antibacterial agents. If present, a personal care composition can include from about 0.001% to about 5%, from about 0.01% to about 2%, from about 0.1% to about 1%, or from about 0.2% to about 0.5%, by weight of the personal care composition, of the one or more antimicrobial agents. In certain examples, zinc pyrithione can be added to the benefit phase, wherein the benefit phase can include an aqueous laponite gel. In certain examples, zinc pyrithione can be added to a benefit phase, wherein the benefit phase comprises about 85% soybean oil and about 15% of a wax or about 80% soybean oil and about 20% of a wax. However, as set forth above, in certain examples, zinc pyrithione and/or other benefit agents can be added to a cleansing phase and/or a benefit phase for deposition onto the skin and/or hair of an individual.

In certain examples, one or more benefit agents or antibacterial agents can be included in cleansing composition. As described, the personal care composition can include a benefit phase. In certain examples, a benefit phase can include one or more benefit agents or antibacterial agents, as described herein. In certain examples, a benefit phase can be substantially free of water. In certain examples, a benefit phase can be substantially free or free of surfactant. Further, in certain examples, a benefit phase can comprise hydrophobic benefit materials. The benefit phase can include, in certain examples, from about 1% to about 50%, from about 5% to about 30%, or from about 10% to about 30%, by weight of the personal care composition, of a hydrophobic benefit material. Additional information relating to the benefit phase is described in detail in U.S. Patent Application Publication No. 2009/0324520. Other suitable benefit agents and antibacterial agents are described in detail in U.S. Pat. No. 6,488,943 (referred to as antimicrobial actives); U.S. Provisional Application Ser. No. 61/523,824; and U.S. patent application Ser. No. 13/438,918, all of which are incorporated herein by reference.

III. Methods of Manufacture

Personal care articles can be manufactured by adding the personal care compositions to an appropriate substrate via a conventional method which can include, but is not limited to, spraying, slot coating, molding (e.g., rotary molding), extrusion, injection, feeding from a hopper and cutting such as by wire cutting, and roll transfer (e.g., pressure roll). A second substrate can then be placed on the first substrate over at least part of a personal care composition. In certain examples, one or more barriers can be formed to define zones within the personal care article. For example, one or more barriers can be applied between applications of personal care compositions. Some personal care articles may also be manufactured by a hot melt method as described in the U.S. Provisional Application Ser. No. 61/620,213 filed on Apr. 4, 2012. Substrates can be sealed together by a conventional sealing method which can include, but is not limited to, heat, pressure, glue, ultrasound, etc. In certain examples, methods of manufacture can include powder filling via vacuum rotary drum molding and/or form-fill seal processes. Optional manufacturing steps can include calendaring to flatten the article as well as drying and cooling.

IV. Methods of Use

A method of cleansing skin and/or hair with a personal cleansing article can include wetting a reusable personal cleansing article and contacting skin and/or hair with the wetted personal cleansing article.

A personal care article can be intended to be wetted with water prior to use. The personal care article can be wetted, for example, by immersion in water or by placing the personal cleansing article under a stream of water. In one example, lather can be generated from the personal care article by mechanically agitating and/or deforming the personal cleansing article either prior to or during contact of the personal cleansing article with the skin and/or hair. The resulting lather can be useful for cleansing the skin and/or hair. During a cleansing process and subsequent rinsing with water, any therapeutic or aesthetic benefit agents can be deposited onto the skin and/or hair. Deposition of the therapeutic or aesthetic benefit agents can be enhanced by physical contact of a substrate with the skin and/or hair as well by the inclusion of one or more deposition aids.

A method for increasing lather can include providing a personal care article having first and second compliant personal care compositions and a first water penetrable substrate. As shown in FIG. 8, a personal care article can include a first compliant personal care composition in a first zone and a second compliant personal care composition in a second zone. Each of the first and second compliant personal care compositions can be in accordance with examples described herein, and in certain examples, the first compliant personal care composition can be the same as the second compliant personal care composition. Further, the first and second zones can be defined by one or more barriers. The method for increasing lather can also include agitating the personal care article. In one example, such agitation can include repeatedly vertically compressing the personal care article such that constant flattening and reforming of the one or more barriers can achieve increased lather production. In certain examples, each of the first and second compliant personal care compositions can be substantially positioned on outer portions of the personal care article, relative to the one or more barriers, such that the personal care compositions can more easily come into contact with the skin and/or hair and water to allow for dissolution. In certain examples, a personal care article can produce about 200 mL or more of lather according to the Piston Lather Test described herein. Lather measurements are shown below in Table 1.

As set forth above, personal care articles used in such a method for increasing lather are described herein. As such, personal care compositions used with the personal care article can include those described above. Similarly, substrates and barriers used for the personal care article can include those described above as well. For example, the barrier can be any of a formed film, a polyurethane sponge, a scrim, a seal, a substrate, and combinations thereof. In one example, a barrier can comprise a bunched substrate. In certain examples, the barrier can act as a spring or pump to facilitate agitation of the personal care article and increase lather production. In such examples, the one or more barriers can be substantially impermeable, while in other examples, the barrier can be substantially permeable (e.g., where both the first and second zones comprise a cleansing composition).

As shown in the example in FIG. 8, one or more barriers can include a first barrier 438, which can define a first zone 430 and a second zone 432, with a first compliant personal care composition 414 in a first zone 430 and a second compliant personal care composition 415 in a second zone 432. The one or more barriers can further include a first interior substrate 434 and a second interior substrate 436, as shown in FIG. 8, such that the first interior substrate 434 can be positioned between the first barrier 438 and the first zone 430 and the second interior substrate 436 can be positioned between the first barrier 438 and the second zone 432.

V. Procedures

A. Water Flux Rate Test

The water flux rate test can measure water permeability of a substrate. Without intending to be limited by theory, water permeability can be a principal determinant of surfactant longevity in a lathering substrate that is used in a presence of water, especially running water. When a surfactant can be present, it can be desirable for the surfactant to lather quickly and profusely, yet be fully depleted at an intended time to signal disposability of a used substrate. If the water flux rate is too low (e.g., zero or near zero), insufficient wetting of the surfactant contained in the substrate can cause lather to start too slowly. On the other hand, if the water flux rate is too high, surfactant can be too readily flushed from the substrate, and a cleansing composition that includes a surfactant will not last long enough.

To measure the water flux rate, with tape or rubber bands, affix a substrate to a bottom of a plastic funnel with the following measurements: a 24 mm inner diameter (i.d.) at an exit, a 145 mm i.d. at a top, 135 mm height (from the top to an onset of a neck), a 20 mm length neck, and a total volume of about 600 mL. Apply sufficient tension to the substrate to ensure that the substrate is completely flat, and no more. Affix tape and rubber bands as close as possible to the exit of the funnel to keep backflow from occurring under water pressure. Next, clamp the funnel in a ring stand over a sink. Measure out 600 mL of water at room temperature in a graduated cylinder. Then, with one hand blocking the funnel exit, pushing against the test substrate, quickly pour the water into the funnel. Once the funnel is completely filled, remove the hand and measure drainage time for the water to evacuate the funnel to a nearest tenth of a second. Stop timing when the water reaches a junction of the neck and a sloped portion of the funnel. Repeat this process 5 times per test substrate and average measurements for each substrate. Substrates which exhibit long drainage times (i.e., about 10 minutes or longer) can be tested by weighing the water drained in a set time period (e.g., 5 minutes) with a funnel full of water and then algebraically determining the flux time for 600 mL of water. Next, measure the water flux rate in the opposite substrate direction (unless the substrate is the same in both directions), and average both results. For substrates with high surface tension against water and small pores (i.e., flow is observed to increase significantly with small amount of surfactant added), add a small but sufficient amount of wetting agent to the water (e.g., Dawn®™ dish liquid), to at least a critical micelle concentration, so that water flows through the substrate unimpeded by wetting forces prior to the test. The water flux rate is expressed in $cm^3/cm^2$-s according to the following equation: Water flux rate=(600 g water)×(1 $cm^3$/g)/((1.2 $cm$)$^2$×(average time in seconds)).

B. Consumption Test

To measure the Consumption Rate of a personal care article or composition, use a rotary tumbler (Lortone, Inc., Seattle, Wash., USA model 33B or equivalent) with a 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter ($\mu$S/cm) and heat in a reservoir beaker to 45° C. Maintain the water supply at the target temperature within 1 degree for the test duration. Add 200.0 g water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water (e.g., if a composition is a conventional bar soap it may transfer paste-like material), the transferred components are to be removed and the article or composition is considered dry when visible transfer is no longer evident. Weigh the article or composition.

Empty and rinse the housing in hot tap water and dry it to complete 1 cycle. Repeat the cycle with the same article 4 more times for a total of 5 cycles. Measure the conductivity of the water reservoir at 30° C., 35° C., 40° C., and 45° C. Using a new article of the same composition, prepare a 1% solution by removing 1.00 grams of its dissolvable chemical composition and adding it to 99.00 grams of water from the reservoir. Dissolve the chemical composition completely, using agitation and heat as necessary. Measure conductivity of the 1% solution at the same 4 temperatures. Prepare a 2% solution in the same way (2.00 grams composition in 98.00 grams water), and measure its conductivity at the same 4 temperatures. Regress the conductivity vs. temperature results for each solution (0%, 1%, and 2%) and obtain the algebraic expressions for each.

For each conductivity-temperature datum for the water in the housing obtained during each cycle, calculate the regressed conductivity for the 0%, 1% and 2% solutions at the temperature measured by the InLab 470 probe for each cycle. Execute a second set of linear regressions for each temperature obtained in the cycles using the solution concentrations (0%, 1%, 2%) as the y (output) and the regressed conductivity values as x (input). Use this second regression at each temperature obtained in each cycle with its paired conductivity value obtained as the input value for x to obtain y, which is the amount of solids of the article dissolved for each cycle. Add the dissolved solids for the 5 cycles and divide by 5 to obtain the Average Dissolved Solids. Multiply the value by 1.67 to obtain the consumption rate of the article, which is based on the relationship between this method and consumption during use of articles in an average ad lib shower by consumers.

C. Substrate and Article Tensile Test

To measure the rigidity of a substrate and/or article, use a Texture Analyzer TA-XT2i (Texture Technologies Corp, NY, USA) tensile tester equipped with at least 5 kg load cell and adjustable upper and lower grips at ambient conditions. Adjust a gauge length of an instrument (grip to grip closest distance) to 50 mm. Cut 1 inch wide, long strips of the personal care article or water insoluble substrate using a precision cutter in a machine direction (MD). (Note: Properties of an article can be measured by separating the personal care composition from the substrates of the article by physical means and cutting 1 inch wide strips of the personal care article with the cleansing composition removed.) If the strips are too short, adjust the gauge length of the instrument to accommodate the strips of the substrate, since the results are expressed in strain. Additionally, if the strips are too narrow, evaluate by normalizing results obtained to a 1 inch width arithmetically.

Affix the strips to grips in the instrument and program the instrument in tensile mode to pull at a rate of 5 mm/second and measure grams-force, using a 2.5 gram trigger to commence recording, for 20 seconds (100 mm). Next, record force at 10% strain in grams (5 mm) and divide the recorded force by 25.4 mm to express a stiffness value in units of grams per mm width (g/mm). Record peak force (grams) and divide the recorded peak force by width to generate the ultimate tensile strength in g/mm width of the article or substrate. For materials which exceed the capacity of a load cell, reduce the width of the strips or increase the load cell capacity to measure the stiffness and ultimate tensile strength.

D. Dissolution Rate Test

Obtain a straight walled glass beaker having an inside diameter (i.d.) of 63 mm and an inside height of 87 mm, (e.g., Pyrex 250 mL (No. 1000) which are widely available). Pour 150 grams of distilled water at ambient temperature (75° F.) into the beaker and add a Teflon® coated magnetic stir bar to the beaker. (Note: The stir bar can be nominally 1.5 inches long×5/16 inches diameter, octagonally-shaped as viewed from the end, and can have a 1/16 in. wide molded pivot ring around its center where the diameter can be about 0.35 in.) Examples of a suitable stir bar can include Spinbar® magnetic stir bars available from Sigma Aldrich Corp. worldwide including Milwaukee, Wis., USA and at www.sigmaaldrich.com.

Measure and record the water conductivity of the water using a conductivity meter (e.g., a Mettler-Toledo Seven-Multi meter with InLab740 probe). (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available (e.g., from DivTech Equipment Co, Cincinnati, Ohio, USA). Center the beaker on the stirrer and turn the stirrer on to obtain a constant rotation speed of 500 rpm to establish a vortex in the water which measures about 3 cm depth from highest point of water at the beaker edge to lowest point of air at the vortex center. Observe the vortex from above to ensure the beaker is centered and that the magnetic stir bar is centered in the vortex. Weigh 1.0 grams of a cleansing composition pressed or formed together as a single unit and add it to the water near the beaker edge but not touching the beaker edge. Begin a timer and allow the water with cleansing composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover (e.g., plastic wrap). Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution ($f$) at each time point by the equation: $f=$(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., $f=0.5$).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a cleansing composition for such articles.

E. Compliance Test

To measure the compliance of a personal care article or composition, use a Texture Analyzer TA-XT2i (Texture Technologies Corp, NY, USA) equipped with at least a 5 kg load cell and a 0.75 inch ball probe at ambient conditions, with the probe zero point at an article top surface using 0.5 gram-force to register a probe height, and a 2 gram-force to commence data collection for both force and distance. Measure a compressive force (kg) at a compression rate of 1 mm/sec over a depth of 5 mm, ensuring that the personal care article or composition form a flat surface over contact area with the ball probe, near the center of the article or composition. Repeat measurements as needed (e.g., at least 3 times) to obtain a representative average value. To determine the compliance of the article or composition divide the maximum observed force (kg) by the maximum compression depth (5 mm). When using a 5 kg load cell some samples may exceed capacity, in this case the maximum compression depth will be less than the set depth of 5 mm, specified in the procedure.

F. Lather Tests

1. Manual Lather Test

Fill a 2000 mL volumetric beaker having approximately a 5 inch inner diameter and being approximately 7.5 inches deep with 600 mL of warm (40° C.) tap water having a water hardness of about 7.5 grains per gallon and conductivity between 100 to not more than 400 microsemens per cm. Fully submerge the personal care article in the water for 5 seconds, remove the article from the water and allow the water to drain into the beaker for 5 seconds. Rub the article on the hands in a back and forth motion for 50 seconds, squeezing and rotating the article from side A to side B at the 10, 20, 30 and 40 second mark. Capture lather from hands and article in the 2000 mL volumetric beaker, removing as much lather from the hands and article as possible. Create an even surface of lather by swirling the beaker in a clockwise manner 3 times to gently agitate the water. Using a ruler, measure the height of the lather from the base of the lather (i.e., top of the water) to the top of the lather, repeating the measurement in 3 locations around the side of the beaker. Average the height values and use to calculate lather volume, using the inner radius of the beaker.

2. Piston Lather Test

Attach the personal care article to the bottom of a modified potato masher (e.g., as commonly sold by OXO)). The potato masher should be modified to hold weight on the upper surface of the mashing grid, such that the combined weight of the potato masher and added weight is 704 g. Attach the upper handle of the masher to an instrument that will provide a vertical motion, resulting in 16 cm of vertical movement at a rate of 10.2 cm/s. However, the machine does not add downward force to the system in the vertical direction. Fill a 2000 mL volumetric beaker having approximately a 5 inch inner diameter and being approximately 7.5 inches deep with 100 mL of warm (40° C.) tap water having a water hardness of about 7.5 grains per gallon and conductivity between 100 to not more than 400 microsemens per centimeter. Place the potato masher into the beaker allowing the cleansing article to soak in the water for 5 seconds. Then, having attached the potato masher to the machine supplying a vertical motion, turn on the machine and carry out 100 up and down vertical translations. Using a ruler, measure the height of the lather from the base of the lather (i.e., top of the water) to the top of the lather, repeating the measurement in 3 locations around the side of the beaker. Average the height values and use to calculate lather volume, using the inner radius of the beaker.

VI. Example

A. Personal Care Composition Examples

Composition Example 1

Prepare a representative personal care composition for a personal care article by combining the following ingredients at 60-70° C. and mixing until homogeneous.

|  | Composition Ex. 1 |
| --- | --- |
| Celvol 523 Polyvinyl alcohol | 7.5 |
| Kuraray PVA 205 | 7.5 |
| Sodium Laureth-1-Sulfate | 26.7 |
| Cocoamidyl propyl betaine | 3.1 |
| PEG 90M | 0.10 |
| Citric Acid | 0.15 |
| Xanthan Gum (Keltrol CG) | 0.25 |
| Perfume | 1.24 |
| Water | QS |

B. Lather Measurements

Lather measurements were taken for each of Article Examples 1-2 for both the Manual Lather Test and the Piston Lather Test, which are described above. Article Examples 1-2 were prepared with 90 grams of the personal care composition described in Composition Example 1 herein. In each of Article Examples 1-2, a first water insoluble substrate was formed from SSRIS-CPM vacuum-formed polyethylene film (from Tredegar, Inc.) and a second water insoluble substrate was formed from ⅛" round vacuum-formed polyethylene film (over 22 Hex base). For each of Article Examples 1-2, a first water penetrable substrate and first interior substrate were formed from another vacuum-formed polyethylene film (40 Hex), and for Article Example 2, a second water penetrable substrate and a second interior substrate were also formed from the same vacuum-formed polyethylene film (40 Hex). Between the first and second interior substrates, a first barrier was formed from a scrim (polyethylene bath implement from Zeca S. R. L.). With respect to the measurements taken for the Piston Lather Test, more lather is produced in Article Example 2, which utilizes the scrim, an internal filler, as a pump.

TABLE 1

|  | Article Example 1 | Article Example 2 |
| --- | --- | --- |
| First Water Insoluble Substrate | F1* | F1* |
| First Water Penetrable Substrate | F2* | F2* |
| Personal Care Composition (PCC) | Compositon Ex. 1 | Compositon Ex. 1 |
| PCC Weight (g) | 90 | 45 |
| First Interior Substrate | F2* | F2* |
| First Barrier | N/A | S1** |
| Second Interior Substrate | N/A | F2* |
| Personal Care Composition (PCC) | N/A | Compositon Ex. 1 |
| PCC Weight (g) | N/A | 45 |
| Second Water Penetrable Substrate | N/A | F2* |
| Second Water Insoluble Substrate | F3* | F3* |
| Total Substrate Weight (g) | 2 | 12 |
| Total Composition Weight (g) | 90 | 90 |
| Comp. Wt. %, by Wt. of Substrate | 4500% | 750% |
| Lather Volume, Manual Test (mL) | 159 | 182 |
| Lather Volume, Piston Test (mL) | 251 | 465 |

*Refers to Code in Formed Films Chart below
**Refers to Code in Scrim Chart below C. Examples of Substrates 1. Formed Films

| Code | Material Description | Caliper and Basis Weight | Pore count/area; and diameter | Water Flux Rate cc/cm$^2$/s | Air Permeability m$^3$/m$^2$/s |
| --- | --- | --- | --- | --- | --- |
| F1 | Vacuum formed polyethylene film, white (SSRIS-CPM, Tredegar Inc.) | 560 microns, 24.5 gsm | 115/cm$^2$ — | 33.8 | 295 |
| F2 | Vacuum formed polyethylene film 40 Hex | 418 microns, 35.8 gsm | 285/cm$^2$ — | 11.5 | 16.2 |
| F3 | Vacuum formed polyethylene film ⅛" round over 22 Hex base | 1330 microns, 37.3 gsm | — | — | — |

Caliper: ASTM D645

Air Permeability: ASTM D737

2. Scrim

| Code | Material Description |
| --- | --- |
| S1 | Polyethlyene or polypropylene bath implement material produced by Zeca S.R.L. |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care article, comprising:
   a) a first compliant cleansing composition in a first zone;
   b) a second compliant cleansing composition in a second zone, wherein each of the zones is defined by one or more barriers; and
   c) a first water penetrable substrate adjacent to the first and second compliant cleansing compositions;
   wherein a total compliant cleansing composition is greater than about 3,500 wt. %, by weight of a total substrate;
   wherein each of the first and second compliant cleansing compositions has a compliance value of about 1.5 kg/mm or less.

2. The personal care article of claim 1, wherein the first and second compliant cleansing compositions are configured to be released at each zone.

3. The personal care article of claim 1, wherein the first compliant cleansing composition is the same as the second compliant cleansing composition.

4. The personal care article of claim 1, wherein the personal care article comprises a top side and a bottom side, wherein the first zone can be located at one of either the top side or the bottom side and the second zone can be located at the remaining side.

5. The personal care article of claim 1, wherein the personal care article comprises a right side and a left side, wherein the first zone can be located at one of either the right side or the left side and the second zone can be located at the remaining side.

6. The personal care article of claim 1, wherein at least one of the one or more barriers is selected from the group consisting of a batting, a formed film, a polyurethane sponge, a scrim, a seal, a second water penetrable substrate, and combinations thereof.

7. The personal care article of claim 6, wherein at least one of the one or more barriers is substantially impermeable.

8. The personal care article of claim 1, wherein the first water penetrable substrate at least partially surrounds each of the first and second compliant cleansing compositions.

9. The personal care article of claim 1, further comprising a second water penetrable substrate adjacent to and in contact with the first water penetrable substrate.

10. The personal care article of claim 9, wherein the second water penetrable substrate at least partially surrounds the first water penetrable substrate.

11. The personal care article of claim 1, wherein the article has a consumption rate of about 1.5 g/use to about 15 g/use.

12. The personal care article of claim 1, wherein the first water penetrable substrate has a water flux rate of about 20 $cm^3/cm^2/s$ or more.

13. The personal care article of claim 1, wherein the total compliant cleansing composition is greater than about 4,000 wt. %, by weight of the total substrate.

14. A personal care article, comprising:
   a) about 4,000 wt. % or more, by weight of a total substrate, of a total compliant personal care composition, wherein a compliant cleansing composition is in a first zone, wherein a compliant personal care composition is in a second zone, wherein each of the zones is defined by one or more barriers, and wherein the compliant cleansing composition and the compliant personal care composition are configured to be released at each zone; and
   b) a first substrate surrounding the compliant cleansing composition and the compliant personal care composition and having a water flux rate of about 0.1 $cm^3/cm^2/s$ to about 60 $cm^3/cm^2/s$; and
   c) a second substrate surrounding the first substrate and having a water flux rate of about 0.1 $cm^3/cm^2/s$ to about 60 $cm^3/cm^2/s$; wherein each of the cleansing composition and the personal care composition has a compliance value of about 1.5 kg/mm or less.

15. The personal care article of claim 14, wherein one of the the personal care composition comprises a benefit phase.

16. The personal care article of claim 14 has a consumption rate of about 0.05 g/use to about 20 g/use.

17. The personal care article of claim 14, wherein the total compliant cleansing composition and personal care composition is greater than about 5,000 wt. %, by weight of the total substrate.

* * * * *